United States Patent
Liang et al.

(10) Patent No.: US 9,741,116 B2
(45) Date of Patent: Aug. 22, 2017

(54) SYSTEM AND METHOD FOR BOUNDARY CLASSIFICATION AND AUTOMATIC POLYP DETECTION

(71) Applicants: Jianming Liang, Scottsdale, AZ (US); Nima Tajbakhsh, Scottsdale, AZ (US); Suryakanth R. Gurudu, Phoenix, AZ (US)

(72) Inventors: Jianming Liang, Scottsdale, AZ (US); Nima Tajbakhsh, Scottsdale, AZ (US); Suryakanth R. Gurudu, Phoenix, AZ (US)

(73) Assignees: Mayo Foundation for Medical Education and Research, Rochester, MN (US); Arizona Board of Regents on Behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 14/914,896

(22) PCT Filed: Aug. 28, 2014

(86) PCT No.: PCT/US2014/053203
§ 371 (c)(1),
(2) Date: Feb. 26, 2016

(87) PCT Pub. No.: WO2015/031641
PCT Pub. Date: Mar. 5, 2015

(65) Prior Publication Data
US 2016/0217573 A1    Jul. 28, 2016

Related U.S. Application Data

(60) Provisional application No. 61/871,722, filed on Aug. 29, 2013.

(51) Int. Cl.
*G06K 9/00* (2006.01)
*G06T 7/00* (2017.01)
(Continued)

(52) U.S. Cl.
CPC ........ *G06T 7/0016* (2013.01); *A61B 1/00009* (2013.01); *A61B 1/31* (2013.01);
(Continued)

(58) Field of Classification Search
USPC ........ 382/100, 103, 106–107, 128–133, 168, 382/173, 181, 199, 203, 209, 219, 232,
(Continued)

(56) References Cited

U.S. PATENT DOCUMENTS 8,184,888 B2 * 5/2012 Lu ........................... G06T 7/143
                                                  382/131
8,369,593 B2 * 2/2013 Peng ...................... A61B 6/032
                                                  378/21

(Continued)

OTHER PUBLICATIONS

International Search Report and Written Opinion under date of mailing of Dec. 5, 2014 in connection with PCT/US2014/053203.
(Continued)

*Primary Examiner* — Seyed Azarian
(74) *Attorney, Agent, or Firm* — Quarles & Brady LLP

(57) ABSTRACT

A system and method is provided for automated polyp detection in optical colonoscopy images. The system includes an input configured to acquire a series of optical images, and a processor configured to process the optical images. Processing steps include performing a boundary classification with steps comprising locating a series of edge pixels using at least one acquired optical image, selecting an image patch around each said edge pixel, performing a classification threshold analysis on each image patch of said edge pixels using a set of determined boundary classifiers,
(Continued)

and identifying, based on the classification threshold analysis, polyp edge pixels consistent with a polyp edge. Processing steps for the processor also include performing a vote accumulation, using the identified polyp edge pixels, to determine a polyp location. The system also includes an output configured to indicate potential polyps using the determined polyp location.

24 Claims, 10 Drawing Sheets

(51) Int. Cl.
  *A61B 1/31*  (2006.01)
  *A61B 1/00*  (2006.01)
  *G06T 5/20*  (2006.01)
  *G06T 7/73*  (2017.01)
  *G06T 7/12*  (2017.01)
  *G06T 7/13*  (2017.01)
  *G06T 7/41*  (2017.01)
  *A61B 6/02*  (2006.01)
  *A61B 5/00*  (2006.01)

(52) U.S. Cl.
  CPC .............. *G06T 5/20* (2013.01); *G06T 7/0012* (2013.01); *G06T 7/12* (2017.01); *G06T 7/13* (2017.01); *G06T 7/41* (2017.01); *G06T 7/73* (2017.01); *A61B 5/4255* (2013.01); *G06T 2207/10016* (2013.01); *G06T 2207/10024* (2013.01); *G06T 2207/10068* (2013.01); *G06T 2207/20024* (2013.01); *G06T 2207/20168* (2013.01); *G06T 2207/30032* (2013.01)

(58) Field of Classification Search
  USPC ....... 382/254, 274, 276, 287, 291, 305, 312; 378/4, 21, 41
  See application file for complete search history.

(56) References Cited

U.S. PATENT DOCUMENTS

2009/0074272 A1* 3/2009 Lu .......................... G06T 7/143
  382/128
2010/0189326 A1* 7/2010 McGinnis ............ G06T 7/0012
  382/131
2011/0206250 A1* 8/2011 McGinnis ............ G06T 7/0012
  382/128

OTHER PUBLICATIONS

Lu et al, "Accurate Polyp Segmentation for 3D CT Colongraphy Using Multi-Staged Probabilistic Binary Learning and Composition Mode", Computer Vision and Pattern Recognitioin, 2008, CVPR 2008, IEEE, retrieved on [Oct. 26, 2014]. Retrieved from Internet: URL: http://stat.fs.edu/-abarbu/papers/PolySegm_CVPR08.pdf.
Ravesteijn et al, "Computer-Aided Detection of Polyps in CT Colonography Using Logistic Regression", IEEE Transactions on Medical Imaging, Vol. 29, No. 1, Jan. 2010. retrieved on [Oct. 26, 2014]. Retrieved from interent: URL: http://homepage.tudelft.nl/h5u3d/papers/Computer_aided_detectin.pdf.

* cited by examiner

SYSTEM AND METHOD FOR BOUNDARY CLASSIFICATION AND AUTOMATIC POLYP DETECTION

CROSS-REFERENCE TO RELATED APPLICATIONS

This application represents the national stage entry of PCT International Application No. PCT/US2014/053203 filed Aug. 28, 2014, which claims priority to U.S. Provisional Application Ser. No. 61/871,722, filed Aug. 29, 2013, both of which are incorporated herein by reference for all purposes.

STATEMENT REGARDING FEDERALLY SPONSORED RESEARCH

N/A

BACKGROUND

The present disclosure relates, generally, to systems and method for processing optical images. More particularly, the disclosure relates to automatic detection of polyps in an optical images.

Colorectal cancer is the second highest cause of cancer-related deaths in the United States with 51,690 estimated deaths in 2012. Colorectal cancer most often begins in the form of small polyps-abnormal growth of the colon surface. The preferred screening method for polyp detection and removal is optical colonoscopy (OC), during which colonoscopist meticulously examine the colon wall to find and remove polyps. Despite many screening and therapeutic advantages, polyp detection with OC remains a challenging task and as evidenced by a recent clinical study, wherein 22% of polyps remained undetected during colon screening with OC. Similar polyp miss rates have also been reported by other clinical studies. To compound the problem, between 4% to 6% of the colorectal cancers diagnosed are thought to be missed on prior colonoscopy. It is therefore important to reduce polyp miss rate as it decreases the incidence and mortality of colorectal cancer.

Computer-aided polyp detection has recently been considered as a tool for reducing polyp miss-rate, where the idea is to highlight regions with suspected polyps during a colonoscopy procedure. Existing algorithms for automatic polyp detection have, thus far, primarily relied upon texture or shape information for detecting polyps. Although texture is a distinguishing characteristic of polyps, merely relying on texture may not address the automatic detection problem. For example, the texture of a polyp becomes fully visible only if the camera captures close shots of the surface of a polyp. This condition is often met when polyps have already been detected by operators, which obviously eliminates the need for computer-aided detection. On the other hand, shape information cannot be considered as a reliable measure since polyps appear in a variety of forms ranging from sessile to peduncular shapes.

Consequently, considering such limitations of previous technological approaches, it would be desirable to have a system and method for accurate and reliable polyp detection in optical colonoscopy images that is shape-independent and mainly captures color variation across the boundary of polyps.

SUMMARY

The present disclosure overcomes the aforementioned drawbacks by providing a system and method that aims to overcome the limitations of shape-based approaches. Specifically, a methodology is introduced that filters out irrelevant boundaries in colonoscopy images by incorporating image context. The boundary removal mechanisms described capture changes in image appearance across polyp boundaries, with minimal effects from texture visibility limitations. In particular, the approach described herein includes a boundary classification stage whereby an edge map from an input colonoscopy image is constructed and refined through a set of boundary classifiers. In addition, a vote accumulation scheme is applied to the refined edge map to localize potential polyps.

In one aspect of the present disclosure, a system for automated polyp detection in optical colonoscopy images is provided. The system includes an input configured to acquire a series of optical images and a processor configured to process the optical images. Processing steps include performing a boundary classification with steps comprising locating a series of edge pixels using at least one acquired optical image, selecting an image patch around each said edge pixel, performing a classification threshold analysis on each image patch of said edge pixels using a set of determined boundary classifiers, and identifying, based on the classification threshold analysis, polyp edge pixels consistent with a polyp edge. Processing steps also include performing a vote accumulation using the identified polyp edge pixels to determine a polyp location. The system also includes an output configured to indicate potential polyps using the determined polyp location.

Another aspect of the present disclosure provides a method for automated polyp detection in optical colonoscopy images. The method includes performing a boundary classification with steps comprising locating a series of edge pixels using at least one acquired optical image, selecting an image patch around each said edge pixel, performing a classification threshold analysis on each image patch of said edge pixels using a set of determined boundary classifiers, and identifying, based on the classification threshold analysis, polyp edge pixels consistent with a polyp edge. The method also includes performing a vote accumulation using the identified polyp edge pixels to determine a polyp location, and generating a report indicative of potential polyps using the determined polyp location.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

The methodology of the present disclosure is based on color variation between polyps and their surrounding tissue. The rationale takes into account that local patterns of color variation across the boundary of polyps differ from the patterns of color variation that occur across the boundary of folds, lumen, and vessels.

Figure 1:
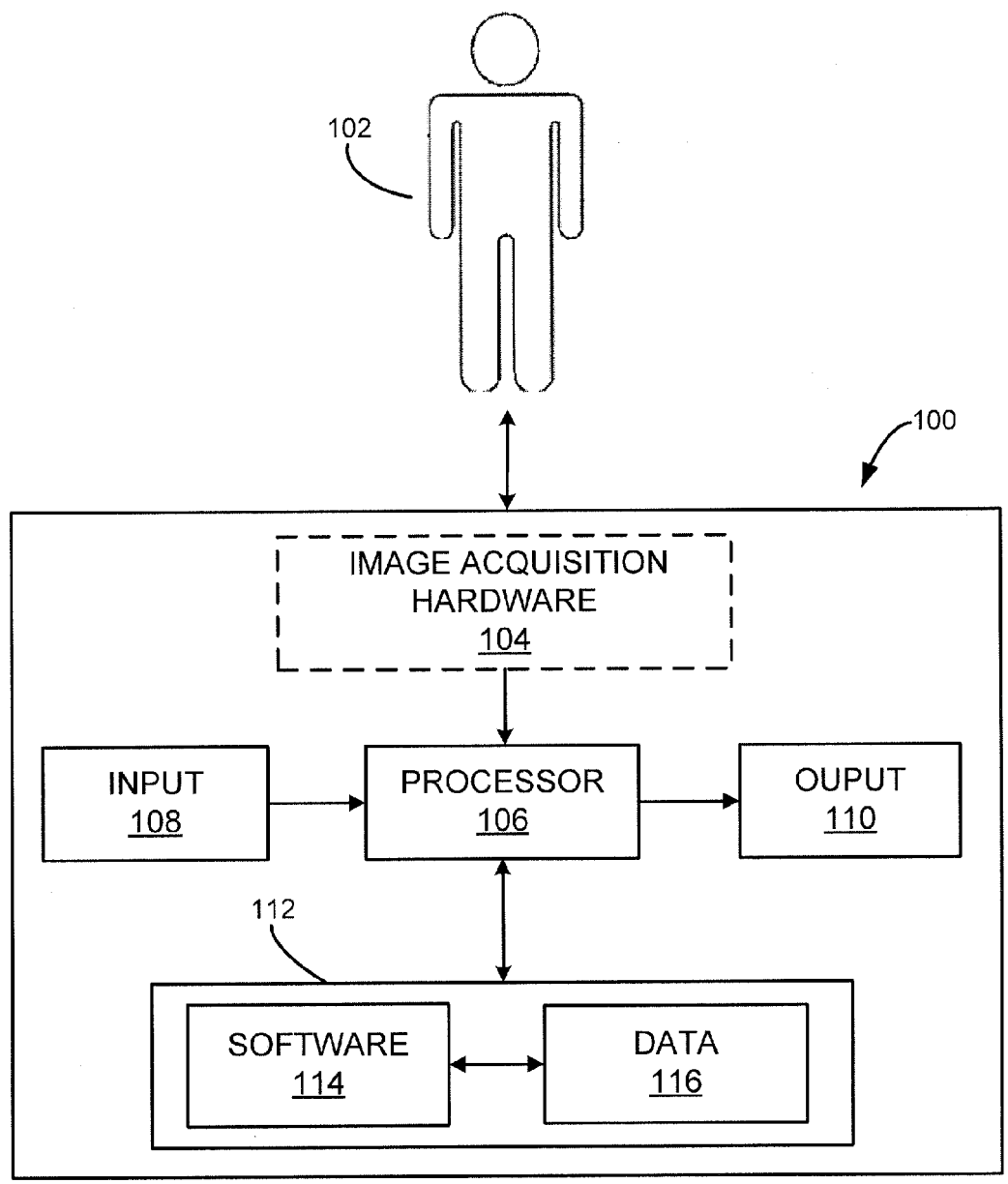
FIG. 1 is a schematic illustration of system for polyp detection in optical colonoscopy images in accordance with the present disclosure.

Turning to FIG. 1, a block diagram is shown of an exemplary polyp detection system 100, which facilitates the detection of polyps on optical images gathered from a subject 102. Polyp detection system 100 generally may include image acquisition hardware 104, a processor 106, an input 108, an output 110, a memory 112, and any device for reading computer-readable media (not shown). The polyp detection system 100 may be, for example, a workstation, a notebook computer, a personal digital assistant (PDA), a multimedia device, a network server, a mainframe or any other general-purpose or application-specific computing device. The polyp detection system 100 may operate autonomously or semi-autonomously, or may read executable software instructions from a computer-readable medium (such as a hard drive, a CD-ROM, flash memory and the like), or may receive instructions from a user, or any another source logically connected to computer or device, such as another networked computer or server. In one embodiment, the polyp detection system 100 may be configured to acquire and analyze optical image data in real-time from a live feed, while a medical procedure is being performed on a subject 102, such as a colonoscopy, and may also be configured to retrieve and analyze optical image data already acquired, and stored in any image data storage location.

Image acquisition hardware 104 may be designed to acquire optical image data continuously or intermittently, for example, during a medical procedure, such as a colonoscopy, and relay optical image data for processing. The image acquisition hardware 104 may require operator direction, input or feedback, or may be designed to operate autonomously.

The processor 106 may be configured to process optical image data, including image data obtained during a medical procedure, such as a colonoscopy. In some configurations, the processor 106 may be designed to process optical images in two stages. In the first stage, a boundary classification may be performed to identify polyp edge pixels consistent with a polyp edge, while in second stage, a vote accumulation is performed, using identified polyp edge pixels, to determine potential polyp locations. In some aspects, a ray back-projection technique may also be performed by the processor 106 to determine a probability for a true detection of the potential polyps.

The processor 106 may be designed to process optical images generated from optical image data, by applying a plurality of color filters. One non-limiting example of a plurality of filters may include a red (R), green (G) and blue (B) filter, often referred to as an RGB filter. Within this example, an HSL or HSV coordinate representation of the RGB model may be used. Other non-limiting examples of color maps include La*b* (or Lab color space). In addition, it is possible to use more than one color map, for instance, RGB+La*b*. Regardless of the filter, map, color space, particular combination of filters, maps, or color spaces, the present invention provides a system and method for polyp detection that leverages the appearance of color variation between polyps and surrounding tissues.

In some aspects, the processor 106 may be configured to determine a set of boundary classifiers using training data, which may be acquired using system 100, and the like, or accessed from a database.

The input 108 may take any shape or form, as desired, for operation of the polyp detection system 100, including the ability for selecting, entering or otherwise specifying parameters consistent with detecting polyps of a requisite or desired size or shape.

The output 110 may take any shape or form, as desired, and may include a visual and/or audio system, configured for displaying, for example, acquired optical images as a result of a medical procedure, such as a colonoscopy, and also configured, for example, to highlight and/or alert an operator of the polyp detection system 100 upon identification of a polyp location with the requisite or desired features.

The memory 112 may contain software 114 and data 116, and may be configured for storage and retrieval of image processing information and data to be processed by the processor 106. In one aspect of the disclosure, the software 114 may contain instructions directed to performing optical image processing for polyp detection. In another aspect of the disclosure, the data 116 may take the form of optical image data.

Figure 2:
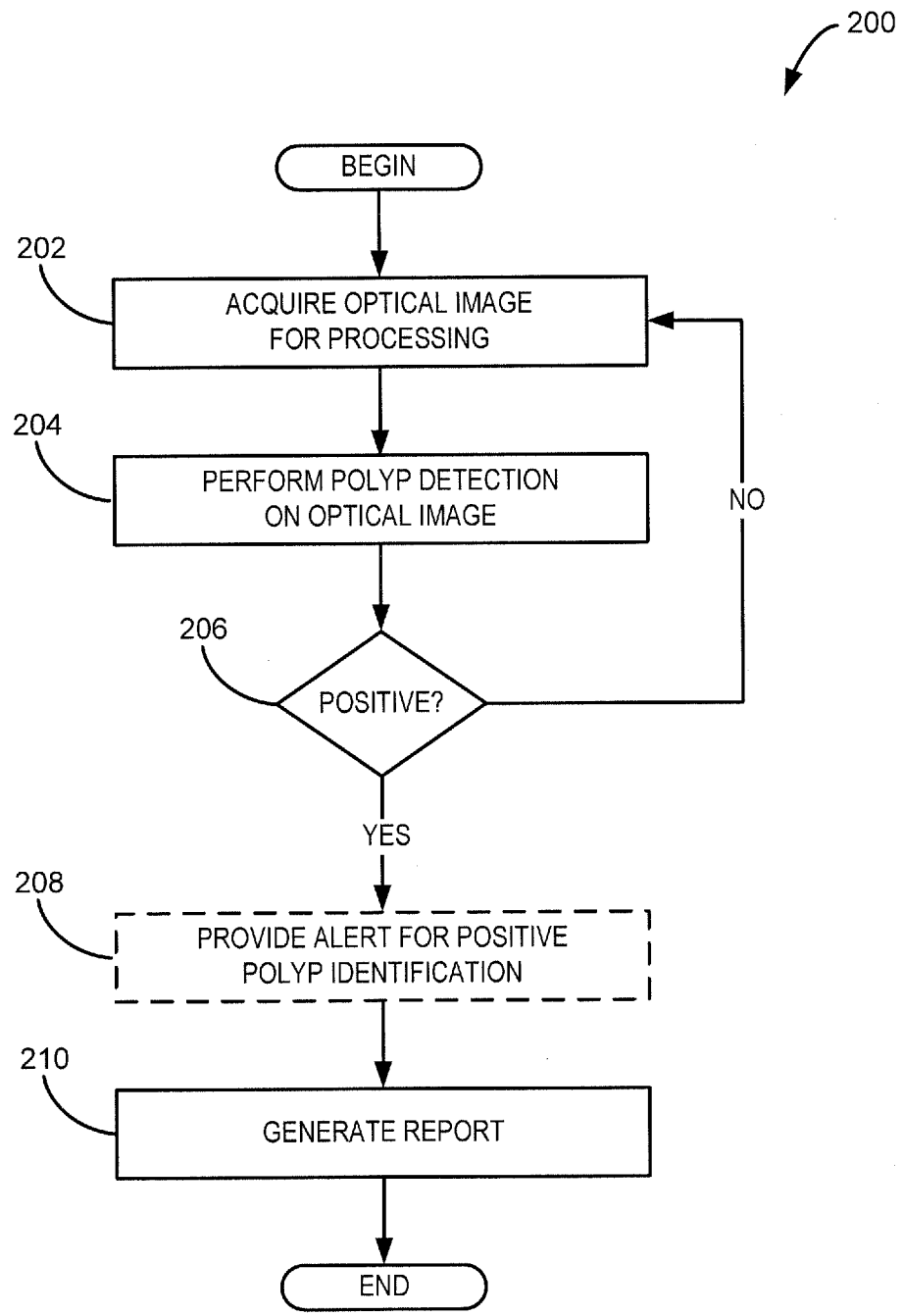
FIG. 2 is a flowchart setting forth examples of steps of a method for operating an automated polyp detection system in accordance with the present disclosure.

Turning to FIG. 2, a process 200 flowchart is shown illustrative of an exemplary method of operation for a polyp detection system 100. The process begins at process block 202, wherein optical image data generated from a live feed, or retrieved from any image data storage location, such as the memory 112, is acquired in the form of an optical image to be operated upon by the polyp detection system 100. At process block 204, a polyp detection is performed on the optical image.

Figure 3:
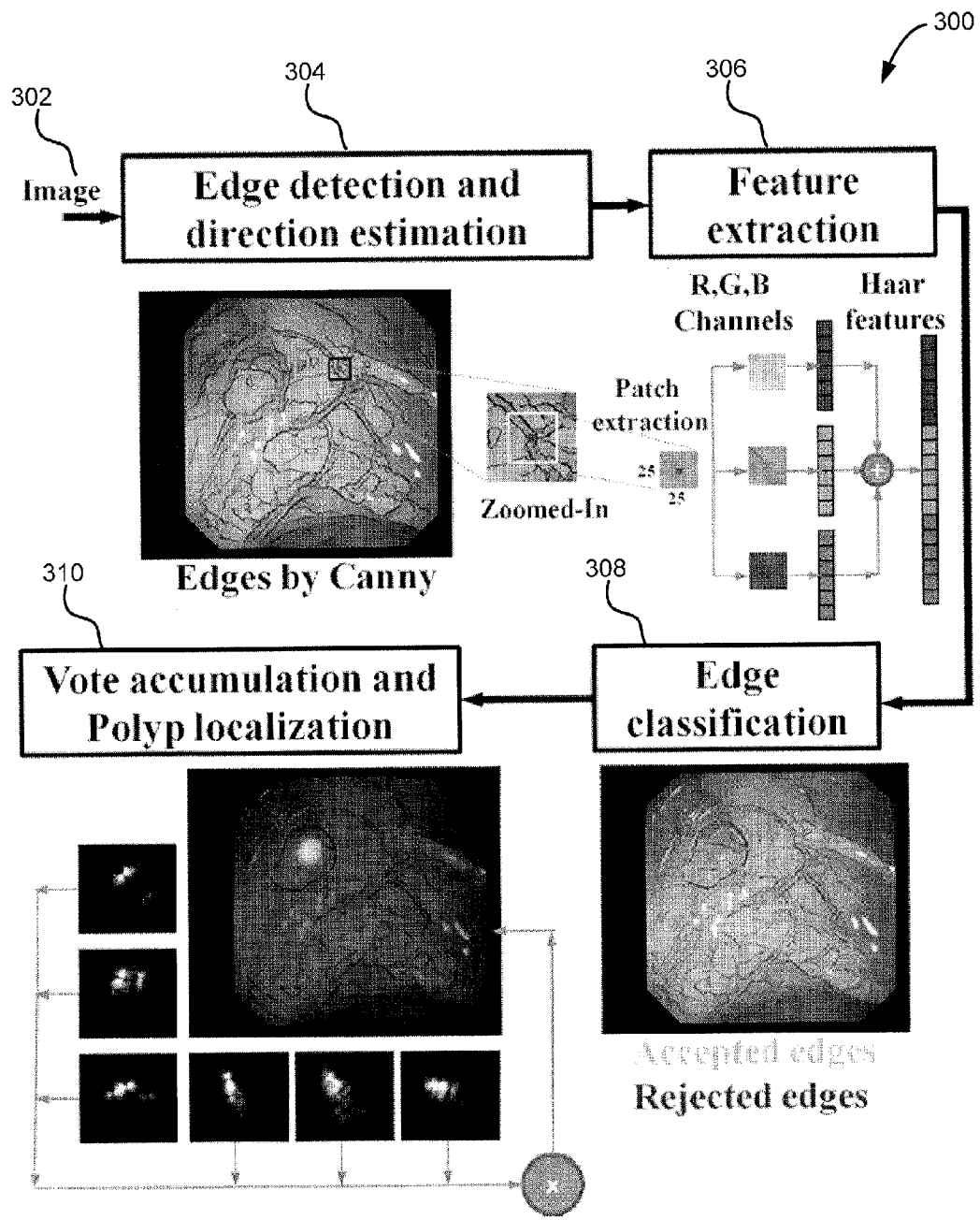
FIG. 3 is a schematic illustration of a process for automated polyp detection in optical colonoscopy images in accordance with the present disclosure.

Illustrating the general steps associated with performing the polyp detection of process block 204, is a flow diagram shown in FIG. 3. The polyp detection process 300 begins with an optical image 302, which undergoes an edge detection and edge direction estimation at process block 304, wherein a crude set of edge pixels are generated using an edge detector. For example, a Canny edge detector may be used, although other edge detectors may also be used. Next, at process block 306, an image patch is formulated around each edge pixel, henceforth identified as a central edge pixel, and each image patch is then grouped into one of, for example, six, categories according to the orientation of the corresponding central edge pixels. Each category of patches is fed to the corresponding classifier. Next, at process block 308, a classifier, such as a random forest classifier, may trained for the patches inside each category. The goal is to classify image patches into polyp and non-polyp categories, where the polyp category contains the patches whose central edge pixels lie on the boundary of polyps, and the non-polyp category contains the patches whose central edge pixels are found on for example, vessels, folds, wrinkles and other objects with strong boundaries in the images. Haar features may be used for training the classifiers. Once complete, at the next process block 310, a vote accumulation and polyp localization step is performed, wherein edges whose corresponding image patches are assigned to the polyp category will be used in the vote accumulation scheme for polyp localization.

Figure 4:
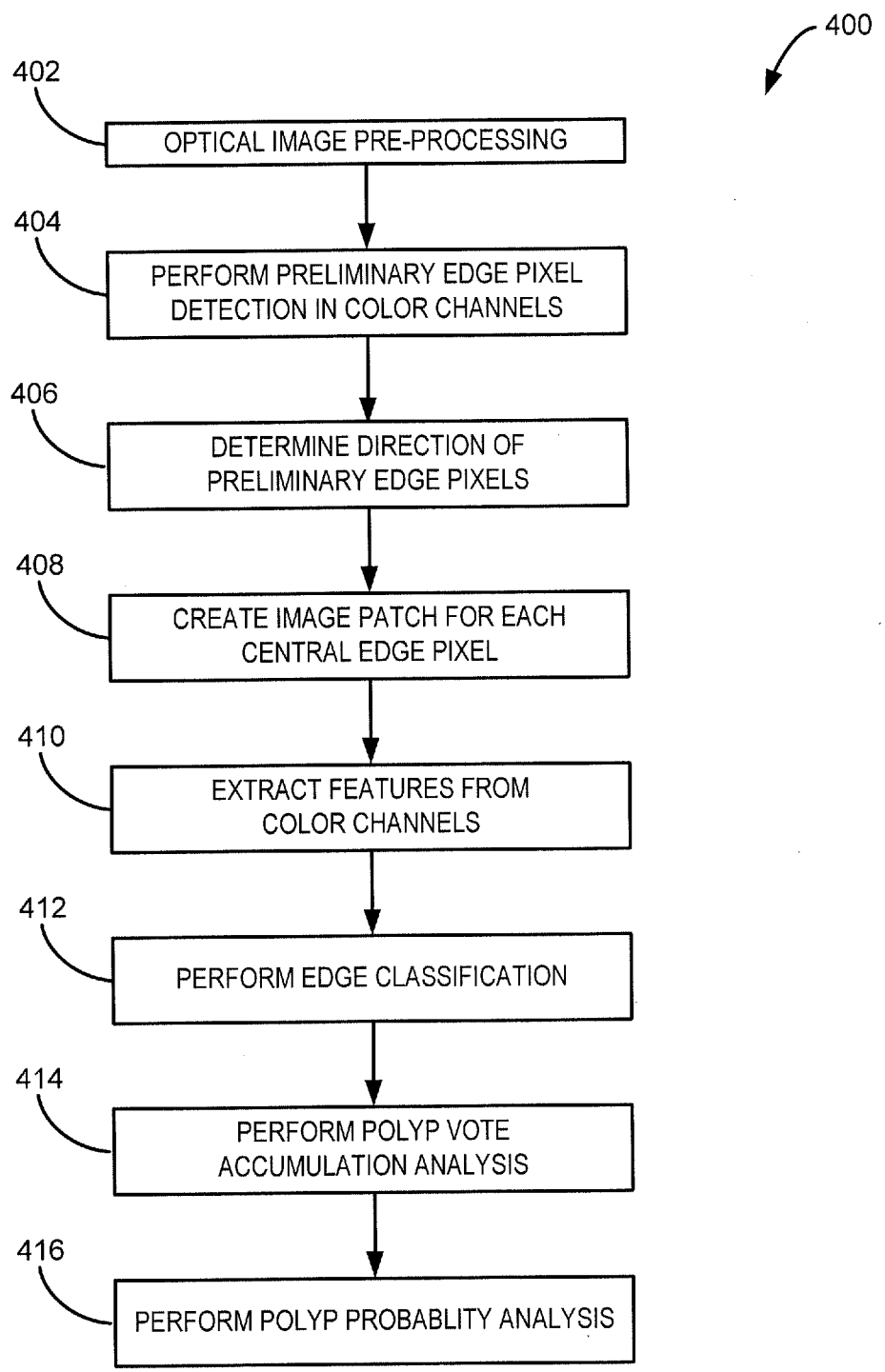
FIG. 4 is a flowchart setting forth examples of steps of method for polyp detection in accordance with the present disclosure.

An example of an implementation of each stage is described with respect to FIG. 4. The polyp detection process 400 begins at process block 402, where a number of pre-processing steps may be applied to the optical image 302, including Gaussian smoothing and/or color filtering. Heavy Gaussian smoothing at process block 402 may remove a large portion of edge pixels including those on the boundaries of polyps. By contrast, slight smoothing may include both prominent and irrelevant edges, which not only may pose a large computational burden on the later stages but also may increase the chance of producing false positives. Hence, a standard deviation of the Gaussian function may be set to 5 ($\sigma_g=5$) to achieve both sensitivity and computational efficiency, although other values are possible.
Edge Detection Then, at process block 404, a crude set of edge pixels is detected, of which only a small fraction may lie on the boundary of polyps. Accurate identification at this point is advantageous, since the desired edge pixels not captured in this stage may not be recovered in later stages. For edge pixel detection, a Canny's method may be used, since it is sensitive enough to capture real polyp edges and specific enough to avoid spurious edges. To extract as many edges as possible Canny's method may be applied to separate color channels, such as red (R), green (G) and blue (B). Of course, other color channels may be used in addition or in alternative to these. Edge segments generated around specular reflections may be removed by identifying regions with high luminance values.
Edge Direction Estimation Next, at process block 406, Canny's algorithm may be used to compute edge direction based on the local estimation of the image gradient in horizontal and vertical directions. However, such estimations are often not accurate, leading to a non-smooth edge direction map. Alternatively, edge direction may be estimated by, for example, performing tensor voting with the assumption that a ball tensor is placed at each edge pixel.

In ball tensor voting, edge direction at a pixel is determined according to the arrangement of the surrounding edge pixels such that the continuation of edge direction is maintained. The locations of neighboring edges determine edge direction at a pixel. It is therefore likely to obtain a consistent or smooth edge direction map. This is in contrast to the traditional edge detection techniques, which only consider a small neighborhood around a pixel, discarding the information of surrounding edges. The only parameter of ball tensor voting is the size of the voting field, which is not a sensitive parameter. A 50×50 voting field may be chosen, although voting fields are also possible, where smaller size could also yield an accurate estimation of edge direction.
Feature Extraction and Classification At process block 408, image patches, for example of size 25×25, are created around each central edge pixel. Then, at process block 410, image patch features are extracted from, for example, the R, G, and B color channels. These features may be Haar features, which compute intensity differences between neighboring horizontal and vertical blocks in various scales and locations in an efficient manner. Therefore, color variation can be efficiently captured for each patch. However, one drawback of Haar features with regard to polyp detection is that they are sensitive to the orientation of edge segments, meaning that different Haar patterns are required to capture color variation across edge segments lying at different orientations. To overcome this drawback, the original classification task may be modified by grouping the image patches into, for example, six, categories according to the orientation of the central edge pixels, where each category may cover ⅙ of the [0, π] range: 0-30°, 31-60°, and so on. The patches inside each category exhibit less diversity, and thus the training process produces less complicated classifiers with more generalization power.

Then, at process block 412, an edge classification is performed. For classification, a random forest classifier may be chosen, given its strong generalization power and its capability to avoid over-fitting of training data. Another distinguishing characteristic of the random forest classifier is the high quality of probabilistic output, leading to advantageous results in a subsequent vote accumulation step, described shortly. At process block 412, image patches with classification confidence less than a threshold, for example 0.5, may be discarded, meaning that their central edge pixels are excluded from the vote accumulation stage. Only edge pixels whose corresponding image patches pass the classification threshold may participate in the vote accumulation stage.
Vote Accumulation for Polyp Localization At the next process block 414, a polyp vote accumulation analysis is performed. In the ideal classification scenario, all non-polyp edge pixels are removed and at process block 412 the arrangement of polyp-edge pixels indicate the location of polyps. However, in practice, a portion of non-polyp edges may pass the classification stage and induce false positives. On the knowledge that false positive edges often appear on elongated and low-curvature edge segments, a vote accumulator scheme that will mitigate the effect of false positive edges on polyp localization may be utilized, as described below.

Figure 5:
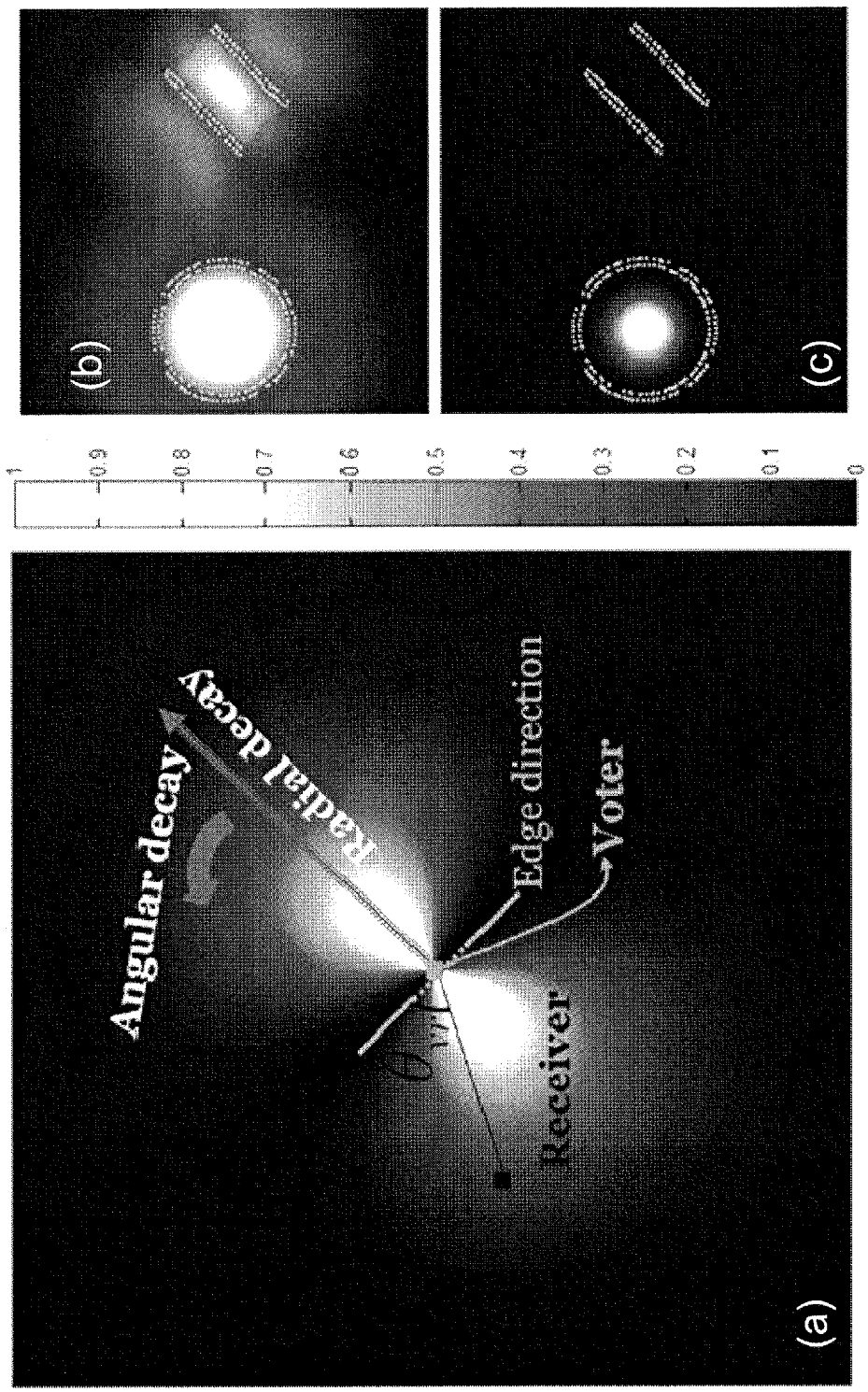
FIG. 5 is a series of illustrations including (a) a geometric illustration of a voting scheme for an edge pixel lying at 135 degrees, with (b) the original voting map and (c) a modified voting map for parallel and circular edges.

Turning to FIG. 5(*a*), in a vote accumulator scheme, every edge pixel casts a scalar vote at each of its neighboring pixels. The magnitude of a vote cast by a voter pixel v at a receiver pixel r is governed by:

$$M_v = C_v \times \exp\left(\frac{-\|v - r\|^2}{\sigma_F^2}\right) \times \sin(\theta_{vr}) \tag{1}$$

where $C_v$ is the probabilistic classification confidence assigned to the voter, the $L^2$-norm measures the Euclidean distance between the voter and receiver pixels, $\sigma_F$ controls the size of voting field, and $\theta_{vr}$ is the angle formed by the voter, receiver, and edge orientation at the voter. The vote accumulation scheme assigns high values to the regions that are fully surrounded by curvy edges, but gives low values to the regions that are partially surrounded by elongated low curvature edges. The exponential and sinusoid terms are radial and angular decay functions, respectively, which (i) limit the contributions from normal edge vectors from very distant structures, (ii) allow vote accumulation even though the edge normals of contributing voters do not intersect at a certain point inside a polyp, and (iii) enable smooth vote propagation, which will be later used in a ray back projection technique to determine the size of a polyp. According to Eqn. 1, pixels with smaller Euclidean distance to the voter and with larger acute angle $\theta_{vr}$ with respect to the edge direction receive votes with higher values.

In one implementation, the only parameter of the vote accumulation scheme is the size of voting field, determined by $\sigma_F$. On one hand, small values of $\sigma_F$ make the voting scheme sensitive to small regions with high vote accumulation, allowing for the detection of small polyps. On the other hand, large values of $\sigma_F$ enable the detection of large polyps but also allow interference from distant voters. In one aspect, $\sigma_F$ may be adjusted for detecting polyps of small and moderate sizes, since large polyps may be more readily detected by colonoscopists. As such, considering that missed polyps are usually 9 to 16 times smaller than the size of images, values $\sigma_F$ may cover a range between 70 and 90, although other values are possible. In another aspect, a multi-scale polyp search approach may also be implemented.

However, in the accumulation scheme described above, votes received at each pixel are accumulated irrespective of the voters' orientation. This implies that the proposed accumulator may be undesirably sensitive to any accumulation of votes, no matter whether they are received from the edge pixels forming a circle or from the edge pixels arranged on some parallel lines. This is a major drawback, since regions delineated by parallel edge segments or by low curvature counters, in general, may not represent polyps., and so high responses in such regions may result in false positive detections.

Recalling that edge pixels are classified into categories according to the angle of their orientation, one way to reduce the sensitivity of the accumulator against parallel or low curvature edge segments, is to perform a modified voting process that is dependent upon edge classification. In one aspect, a voting process may be performed for each classification category, where during each voting process, the edge pixels corresponding to at least one specific category is allowed to vote. Once all votes are cast, an accumulator adds up the votes received at each pixel and generates a voting map for each group of the edges. As illustrated by process block 310 of FIG. 3, the resultant number of, for example, 6, voting maps may be then combined to form a modified map indicative of the location of a polyp, wherein regions with high values are the result of adequate responses from each individual voting map category. Mathematically, this may be expressed as:

$$\operatorname{argmax}_{x,y} \Pi_i^N \Sigma_{v \in V_i} M_v(x,y) \qquad (2)$$

where N represents the number of voting categories.

The necessity of edge grouping prior to vote casting and accumulation is demonstrated in FIG. 5(b), where a comparison is shown between voting maps of edge pixels arranged on a circle and edge pixels lying on two parallel lines, without edge grouping. As may be seen, votes are accumulated both inside circular edges, which is likely desirable for polyp identification, and between the parallel lines, which is likely undesirable for polyp identification.

However, preceding the voting scheme with edge grouping may mitigate undesirable vote accumulation between low curvature edge segments. This is illustrated in FIG. 5(c), which illustrates the effect of the modified voting map for the same edge pixels. Regions surrounded by low curvature boundary (for example, parallel edges) receive low values, because their surrounding edge pixels can only contribute to a small fraction of the voting maps, whereas high values are assigned to the region inside the circular edges.

Returning to FIG. 4, upon the completion of a vote accumulation step, at process block 416, a polyp probability analysis is performed to limit false polyp detections. In one aspect, a ray back-projection technique may be implemented to identify the probability a probability for a true detection of the potential polyps. This approach is illustrated by an example shown in FIG. 6, wherein rays are cast from a detection point 600 outward in all possible directions and the fraction of rays hitting the positively classified edges within a pre-determined radius is computed. The higher the fraction, the more likely a detection will be a polyp.

In this ray back-projection approach, it would be advantageous that the pre-determined radius be large enough to include polyp boundaries and short enough to exclude false positive edges, since short or long radii may underestimate or overestimate the polyp likelihood. Therefore, in one aspect, a way to determine the search radius is to examine the change in vote accumulation along each radial ray.

Figure 6:
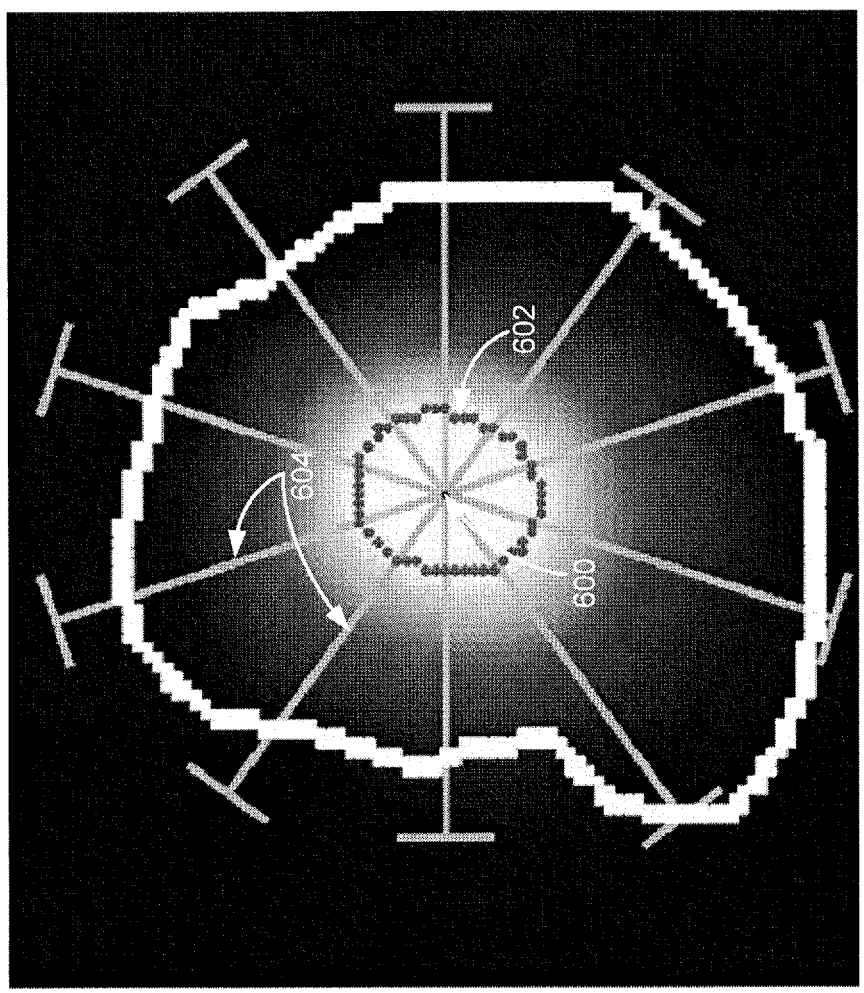
FIG. 6 is a polyp image example illustrating a ray back-projection method.

In general, moving from the detection point 600 outward, vote accumulation decreases in a Gaussian-like fashion initially and is subsequently followed by rapid decrease. Experiments reveal that if the vote accumulation decay follows the slow Gaussian pattern, a polyp boundary may be reached within 3 standard deviations, namely, $3\sigma_\theta$, of the Gaussian function. Therefore, in one aspect, the decay signal at angle $\theta$ may be modeled with a Gaussian function with a corresponding search radius set to be, say, $3\sigma_\theta$. Given two points on a decay signal $\{p_1, p_2\}$ and their corresponding vote accumulations $\{v_1, v_2\}$, $\sigma_\theta$ may be obtained as follows:

$$\sigma_\theta = \frac{\|p_2 - p_1\|^2}{-\ln(v_2/v_1)} \qquad (3)$$

where $p_1$ contains image coordinates of the detection point and $p_2$ contains image coordinates of a point on the signal within, for example, 70% of the maximum vote accumulation (i.e. $v_2/v_1 \geq 70\%$), namely the range in which the decay signals exhibit a Gaussian-like decrease. In the example of FIG. 6, dot points 602 refer to locations where the decay signal has reached 70% of maximum vote accumulation, and lines 604 show search radii for a subset of radial rays. Once search radii for all rays are determined, the probability of being polyp may be computed as follows:

$$p(polyp|R_\theta|_{\theta=0}^{359}) = \frac{1}{180} \sum_{\theta=0:179} R_\theta \oplus R_{\theta+180} \qquad (4)$$

where $R_\theta$ is an indicator variable that generally takes a value of 1 if the ray at angle $\theta$ hits at least one positive edge or 0 otherwise. Eqn. 4 aims to treat polyps with complete and partial boundaries equally, thus enabling detection of partially appearing polyps that may be located behind the folds or at image boarders.

The voting scheme outlined above has at least two major advantages over traditional Hough transform (HT) methods. First, while HT is valued for detecting shapes with specific parametric model (e.g., circle and ellipse), the approach implemented in this disclosure naturally handles a variety of curvy shapes with local convex and concave boundaries. Second, HT does not produce a normalized output, which complicates a classification threshold for accepting or rejecting polyp candidates, By contrast, this limitation is properly handled by the above-described ray back-projection technique.

Turning now back to FIG. 2, at decision block 206 of FIG. 2, if a polyp is not detected, the above process may be repeated, wherein a next optical image is acquired at process block 202, and so on, as desired or as additional optical images are available. However, if a polyp is positively identified, then, at process block 208, an alert or signal may be provided to an operator, indicating a positive polyp identification. The alert or signal may take any shape, form, or sound. Subsequently, at process block 210, a report is generated, which may take any shape or form.

Specific examples are provided below, illustrative of the above-described polyp detection method. These examples are offered for illustrative purposes only, and are not intended to limit the scope of the present invention in any way. Indeed, various modifications of the invention in addition to those shown and described herein will become apparent to those skilled in the art from the foregoing description and the following example and fall within the scope of the appended claims.

EXAMPLE

A CVC-ColonDB database was used to evaluate the methodology described in the current disclosure, where CVC-ColonDB is the only publicly available polyp database, consisting of 380 colonoscopy images selected from 15 short colonoscopy videos. Each image of the database contained a colorectal polyp, including pedunculated, sessile, and flat polyps. In the following, each stage of the proposed polyp detection method was evaluated and results were presented.

Edge Detection

Figure 7:
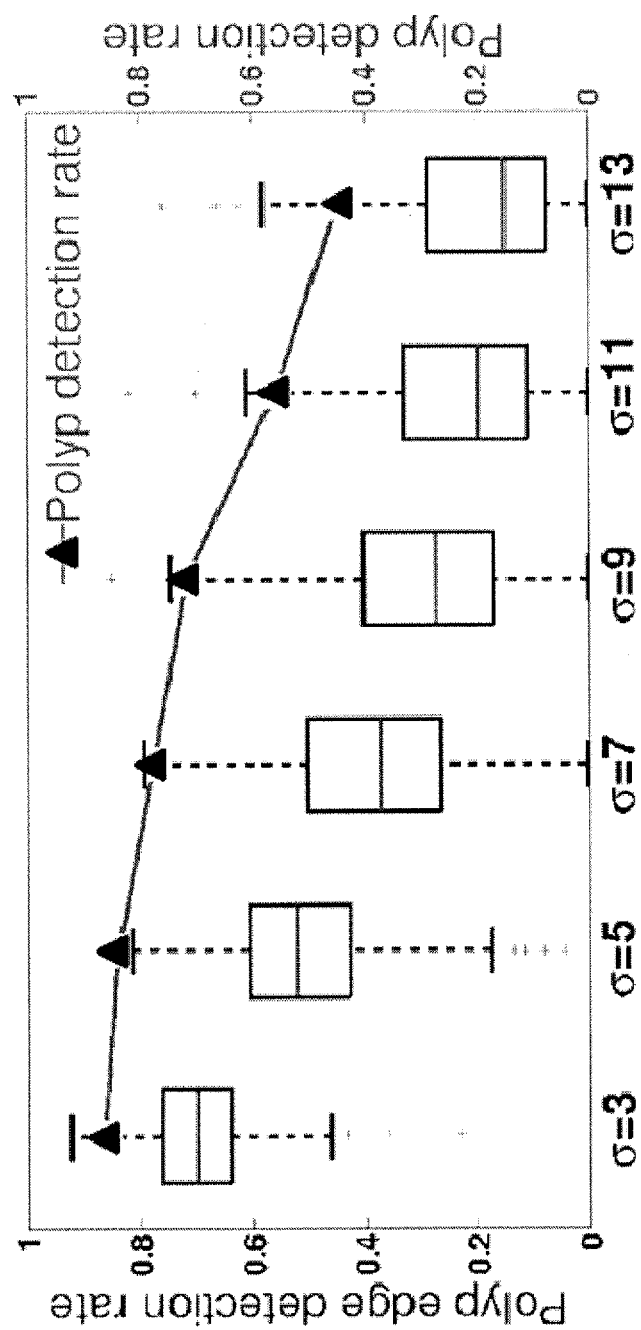
FIG. 7 is a graph showing the effect of Gaussian smoothing on the sensitivity of Canny edge detector and the sensitivity of voting scheme.

Edge detection yields a crude set of candidate edges. The upper and lower thresholds of the Canny algorithm were computed automatically relative to the highest value of the gradient magnitude of the image. To determine the degree of Gaussian smoothing, $\sigma_g$, experiments were conducted to investigate how changes in Gaussian smoothing affect the percentage of polyp edges detected by the Canny algorithm in each of the 300 images. The results are shown in FIG. 7. Each box plot displays the distribution of polyp edge detection rates for the 300 images. As seen, the larger the $\sigma_g$, the lower the median of polyp edge detection rate. Since the polyp edges missed during the edge detection stage may not be recovered in the later stages, the Gaussian smoothing was chosen to be $\sigma_g=3$, which achieved a high level of sensitivity against polyp edges. FIG. 7 also shows the fraction of images for which the maximum of voting map falls inside a polyp. As seen, the detection rate decreases as $\sigma_g$ increases. It may be noted that the larger values of $\sigma_g$ tend to exclude more polyp edges from the classification stage, leading to less accurate polyp localization.

Edge Classification

Figure 8:
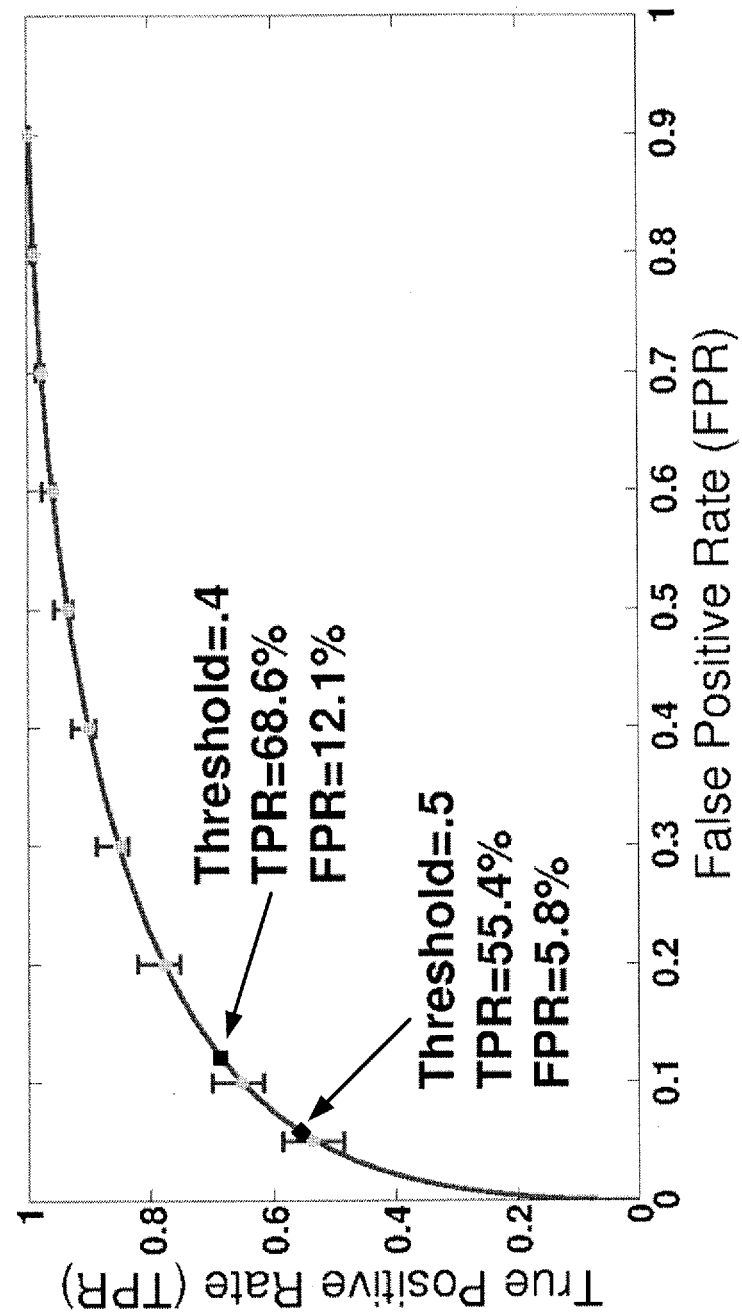
FIG. 8 is a graph showing an overall receiver operating characteristic ROC curve for a 5-fold cross validation.

A five-fold cross validation was implemented to use the totality of 300 images for performance evaluation. For each training set, a stratified sampling was implemented to form the set of training positive and negative image patches. Such a sampling is advantageous given the imbalanced nature of classification task and the very large number of polyp and non-polyp edges. The training image patches were then grouped into six categories and a random forest classifier was trained in each category of the patches. The classifiers were then applied to the test images in order to classify all the edge pixels returned by the Canny algorithm. The random forest classifiers were constructed with 30 decision trees and randomness was injected by randomly selecting a subset of features at each node of the trees. The polyp detector was trained for each training set and then applied to the corresponding test set to count true and false detections. A receiver operating characteristic (ROC) curve was obtained for all test folds by putting together all the probabilistic outcomes generated by the six classifiers on 5 test folds. In this way, 30 possible ROC's (6 ROC's for each of the 5 folds) were combined into a single plot, as shown in FIG. 8. The default classification threshold was used to removed negative edges.

Voting Scheme

Figure 9:
FIG. 9 shows positive polyp detection results for images obtained from CVC-ColonDB database.
Figure 10:
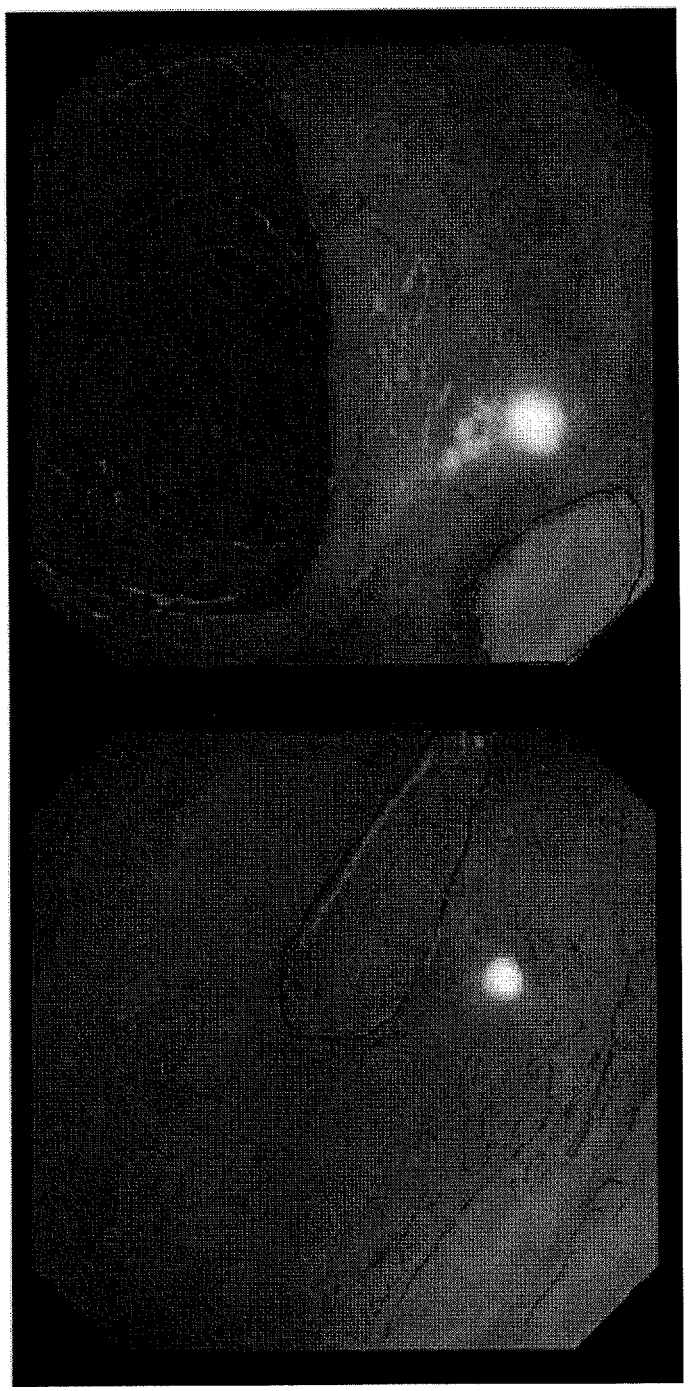
FIG. 10 shows negative polyp detection results for images obtained from CVC-ColonDB database.

The method of the present disclosure detected 262 out of 300 polyps and produced 40 false detections. FIG. 9 shows detection results for images from the CVC-ColonDB database, illustrating true detections. The voting maps are shown superimposed on the colonoscopy images for better visualization. For each image, the detection point is the maximum of the voting map. The false detections produced by voting scheme occurred mostly due to aggressive edge classification or inadequate clear boundary between polyps and their surrounding area. FIG. 10 shows examples of false detections wherein the maxima of the voting maps fall outside the polyp regions.

Polyp Detection

Precision and recall values were obtained by changing a threshold on the polyp likelihood and calculating the fraction of true and false detections at each threshold. A detection was considered a "true detection" if the maximum of the voting map passed the classification threshold and fell inside the ground truth contour provided by the database. Since the polyp detection method placed the maxima of the voting maps in 262/300 images, it achieved up to 86% recall. Table 1 shows precision and recall values at 4 operating points for the polyp detection method disclosed compared to previous work. As seen, the obtained results are promising and outperform the state-of-the-art.

TABLE 1

Precision and recall comparison between the current polyp detection method and sector accumulation-depth of valleys accumulation (SA-DOVA) approach.

| | Precision | |
|---|---|---|
| Recall | Current Method | SA-DOVA (previous work) |
| 50% | 90% | 92% |
| 70% | 89% | 65% |
| 86% | 86% | 60% |
| 100% | — | 50% |

In summary, colorectal cancer most often begins as abnormal growth of the colon wall, commonly referred to as polyps. It has been shown that the timely removal of polyps with optical colonoscopy (OC) significantly reduces the incidence and mortality of colorectal cancer. However, polyp detection with OC is a challenging task and as reported, many polyps remain undetected. Computer-aided detection may offer promises of reducing polyp miss-rate.

The current disclosure describes a system and method that systematically exploits the unique appearance of polyp boundaries to identify polyps. This approach can accommodate large variations in polyp shapes and is designed to perform polyp detection from partially identified boundaries, while eliminating parallel edge configurations. The method was evaluated on 300 images from a publicly available database, containing colorectal polyps of different shapes and scales, from which 262 out of 300 polyps were accurately detected. The results outperform the state-of-the-art and demonstrate the feasibility and promises of a boundary classification approach for automatic polyp detection.

The present invention has been described in terms of one or more preferred embodiments, and it should be appreciated that many equivalents, alternatives, variations, and modifications, aside from those expressly stated, are possible and within the scope of the invention.

We claim:

1. A system for automated polyp detection in optical colonoscopy images comprising:
   an input configured to acquire multiple optical images;
   a processor configured to process said optical images with steps comprising:
   i. performing a boundary classification with steps comprising:
      a. locating a series of edge pixels using at least one acquired optical image;
      b. selecting an image patch around each said edge pixel;
      c. performing a classification threshold analysis on each image patch of said edge pixels using a set of determined boundary classifiers;
      d. identifying, based on the classification threshold analysis, polyp edge pixels consistent with a polyp edge;
   ii. performing a vote accumulation using the identified polyp edge pixels to determine a polyp location;
   an output configured to indicate potential polyps using the determined polyp location;
   wherein performing the classification threshold analysis of said image patches comprises a comparison between said image patches and a series of image patterns; and
   wherein each of the series of image patterns comprises a plurality of categories, with each category spanning an angular orientation consistent with ⅙ of a range between 0 and $\pi$.

2. The system of claim 1, wherein the processor is further configured to apply a color filter to create a plurality of color filtered images for each optical image.

3. The system of claim 2, wherein said color filter comprises a red filter, a green filter, and a blue filter.

4. The system of claim 1, wherein locating said edge pixels comprises applying a Canny edge detection algorithm.

5. The system of claim 1, wherein the processor is further configured to estimate an edge direction for each of the series of said edge pixels.

6. The system of claim 5, wherein each edge direction is estimated by a tensor voting with a ball tensor placed at a location of each said edge pixel.

7. The system of claim 1, wherein each image patch comprises a plurality of pixels arranged such that the said edge pixel is positioned central to the image patch.

8. The system of claim 1, wherein identifying polyp edge pixels consistent with a polyp edge comprises applying a random forest classifier.

9. The system of claim 1, wherein the processor is further configured to determine a classification confidence for the identified polyp edge pixels.

10. The system of claim 1, wherein for each edge pixel in the optical image, said vote accumulation is performed for a plurality of categories, generating a plurality of voting maps.

11. The system of claim 10, wherein the plurality of voting maps are combined according to:

$$\mathrm{argmax} \Pi_i^N \Sigma_{v \in V_i} M_v$$

where N is a number of categories, $M_v$ is a vote accumulation intensity, and v is a voter in a voting category, $V_i$.

12. The system of claim 1, wherein the processor is further configured to perform a ray back-projection technique to indicate a probability for a true detection of the potential polyps.

13. A method for automated polyp detection in optical colonoscopy images comprising:
   i. performing a boundary classification with steps comprising:
      a. locating a series of edge pixels using at least one acquired optical image;
      b. selecting an image patch around each said edge pixel;
      c. performing a classification threshold analysis on each image patch of said edge pixels using a set of determined boundary classifiers;
      d. identifying, based on the classification threshold analysis, polyp edge pixels consistent with a polyp edge;
   ii. performing a vote accumulation using the identified polyp edge pixels to determine a polyp location;
   iii. generating a report indicative of potential polyps using the determined polyp location
   wherein performing the classification threshold analysis of said image patches comprises a comparison between said image patches and a series of image patterns; and
   wherein each of the series of image patterns comprises a plurality of categories, with each category spanning an angular orientation consistent with ⅙ of a range between 0 and $\pi$.

14. The method of claim 13, the method further comprising applying a color filter to create a plurality of color filtered images for each optical image.

15. The method of claim 14, wherein said color filter comprises a red filter, a green filter, and a blue filter.

16. The method of claim 13, wherein locating said edge pixels comprises applying a Canny edge detection algorithm.

17. The method of claim 13, the method further comprising estimating an edge direction for each of the series of said edge pixels.

18. The method of claim 17, wherein each edge direction is estimated by a tensor voting with a ball tensor placed at a location of each said edge pixel.

19. The method of claim 13, wherein each image patch comprises a plurality of pixels arranged such that the said edge pixel is positioned central to the image patch.

20. The method of claim 13, wherein identifying polyp edge pixels consistent with a polyp edge comprises applying a random forest classifier.

21. The method of claim 13, the method further comprising determining a classification confidence for the identified polyp edge pixels.

22. The method of claim 13, wherein for each edge pixel in the optical image, said vote accumulation is performed for a plurality of categories, generating a plurality of voting maps.

23. The method of claim 22, wherein the plurality of voting maps are combined according to:

$$\mathrm{argmax} \Pi_i^N \Sigma_{v \in V_i} M_v$$

where N is a number of categories, $M_v$ is a vote accumulation intensity, and v is a voter in a voting category, $V_i$.

24. The method of claim 13, the method further comprising performing a ray back-projection technique to indicate a probability for a true detection of the potential polyps.

* * * * *